United States Patent

Roscher et al.

Patent Number: 5,973,176
Date of Patent: Oct. 26, 1999

[54] HYDROLYZABLE, FLUORINATED SILANES, METHOD OF THEIR PRODUCTION AND THEIR USE FOR PRODUCING SILICIC ACID POLYCONDENSATES AND HETERO SILICIC ACID POLYCONDENSATES

[75] Inventors: Christof Roscher; Michael Popall, both of Wuerzburg; Birke-E. Olsowski, Veitshoechheim, all of Germany

[73] Assignee: Fraunhofer-Gesellschaft zur Foerderung der angewandten Forschung e.V., Munich, Germany

[21] Appl. No.: 08/832,283

[22] Filed: Apr. 3, 1997

[30] Foreign Application Priority Data

Apr. 4, 1996 [DE] Germany .................. 196 13 650

[51] Int. Cl.$^6$ .................. C07F 7/08; C07F 7/10; C07F 7/18

[52] U.S. Cl. .................. 556/440; 556/10; 556/12; 556/438; 556/439; 556/482; 556/489; 549/215; 106/287.1; 106/287.11; 106/287.13; 106/287.16

[58] Field of Search .................. 556/489, 482, 556/10, 12, 438, 439, 440; 549/215; 106/287.1, 287.11, 287.13, 287.16

[56] References Cited

U.S. PATENT DOCUMENTS

| 3,269,928 | 8/1966 | Haszeldine et al. | 556/489 |
| 3,423,445 | 1/1969 | Holbrook et al. | 556/482 |
| 5,693,261 | 12/1997 | Krzystowczyk et al. | 56/489 X |

Primary Examiner—Paul F. Shaver
Attorney, Agent, or Firm—Karl Hormann

[57] ABSTRACT

The invention relates to hydrolyzable fluorinate silanes, methods of their production and of their use for producing silicic acid polycondensates and hetero silicic acid polycondensats The silanes in accordance with the invention are of the general formula: $\{[R'-(Y)_e]_{c+1}(C_6F_{4-c})(C_6F_4)_d\}_f SiR_a X_b$ (I) in which the groups and indices are identical or different and have the following meaning:

R=alkyl, alkenyl, aryl, alkylaryl or arylalkyl, substituted if required, each with 1 to 15 carbon atoms, whereby the groups may be interrupted by oxygen or sulfur atoms, ester, carbonyl, amide or amino groups;

R'=I, Br, Cl (if d≠0), F (if d≠0), H (if X≠H or R≠methyl or e=1) or an organic group with 1 to 50 carbon atoms;

X=hydrogen, halogen except fluorine, hydroxy, alkoxy, acyloxy, alkylcarbonyl, alkoxycarbonyl or NR"$_2$, with R"=hydrogen, alkyl or aryl;

Y=O, S, NH or NR', where R' is an organic group with 1 to 50 carbon atoms;

a=0, 1 or 2;

b=1, 2 or 3;

c=0 or 1;

d=0 to 9;

e=0 or 1;

f=1, 2 or 3, with a+b+f=4.

18 Claims, No Drawings

HYDROLYZABLE, FLUORINATED SILANES, METHOD OF THEIR PRODUCTION AND THEIR USE FOR PRODUCING SILICIC ACID POLYCONDENSATES AND HETERO SILICIC ACID POLYCONDENSATES

The invention relates to hydrolyzable, fluorinated silanes, methods of their production as well as to their use for producing silicic acid polycondensates and hetero silicic acid polycondensates.

Hydrolyzable organically modified silanes are used widely in the production of scratch-proof coatings for many different substrates, for the production of fillers, adhesive and caulking compounds or of formed articles. To this end, such silanes are hydrolytically condensed either by themselves, in mixtures or in the presence of further hydrolyzable and/or condensible compounds, any final curing being carried out by polymerization, poly-addition or polycondensation, usually thermically, photochemically, covalently nucleophilic or by redox induction.

Thus, scratch-proof coatings are known, for instance, from German patent DE 3,407,087, which are formed by hydrolytic condensation of a mixture, consisting, among others, of a hydrolyzable titanium or zirconium compound and of a hydrolyzable organo-functional silane $R'_m(R''Y)_nSiX_{(4-m-n)}$, wherein R' may, for instance, be alkyl or alkenyl, R'' may be alkylene or alkene and X is a hydrolyzable group. The disadvantages of these coatings are, however, their insufficient optical properties, so that their use for optical or opto-electronic applications is possible to a limited extent only.

From German patent DE 3,536,716 A1 adhesive and caulking compounds are known, for instance, which have been made by hydrolytic condensation of one or more organo-silanes of the general formula $R_m SiX_{4-m}$ and, where required, of one or more compounds $SiX_4$ and/or $R_n(R''Y)SiX_{4-n-p}$, wherein R and R'' may, for instance, be Alkyl, alkenyl, aryl, alkylaryl, arylalkyl, alkenearyl or arylalkene, X may be hydrogen, halogen, hydroxy, alkoxy or acyloxy, and Y may be, for instance, a halogen or a substituted, if required, amino, amide, aldehyde, alkylcarbonyl, carboxy, hydroxy, mercapto or cyano group.

Again, the disadvantage of these adhesive and caulking compounds is their insufficient optical properties, so that their use for optical and opto-electronic applications is also only possible to a limited extent.

(Polyfluorophenyl)-silanes have been described by M. Weidenbruch (Chemiker-Zeitung, Vol. 97 (1973), No. 3, pp. 116–122). However, these silanes are hydrolyzable to a limited extent only and, moreover, have no functionalities in their molecule so that these silanes are wholly unsuitable for the production of hetero silicic acid polycondensates.

Therefore, it is a task of the instant invention to provide organically modified silanes which are hydrolyzable, which by themselves, in mixtures or together with other hydrolyzable and/or condensible compounds may be processed into scratch-proof coatings, fillers, adhesive or caulking compounds, into formed articles or imbedding materials. These silanes are to be universally applicable, and they are to be incorporable into an inorganic-organic compound system, i.e. an inorganic-organic network. Furthermore, these silanes are by themselves, in mixtures or together with other hydrolyzable and/or condensible compounds to yield hetero silicic acid polycondensates of good adhesive and temperature properties and good optical attenuation values so that these hetero silicic acid polycondensates are suitable for optical or opto-electronic applications.

The task is accomplished by silanes of formula I $$\{[R'-(Y)_e]_{c+1}(C_6F_{4-c})(C_6F_4)_d\}_f SiR_aX_b \qquad (I)$$

in which the groups and indices may be identical or different and have the following meaning:

R=If required substituted alkyl, alkenyl, aryl, alkyl-aryl or arylalkyl each with 1 to 20 carbon atoms, whereby these groups may be interrupted by oxygen or sulfur atoms, by ester, carbonyl, amide or amino groups;

R'=I, Br, Cl (if d≠0, F (if d≠0), H (if X≠H or R≠methyl or e=1) or an organic group with 1 to 50 carbon atoms;

X=hydrogen, halogen except flouurine, hydroxy, alkoxy, acyloxy, alkyl-carbonyl, alkoxycarbonyl or NR''$_2$, with R''=hydrogen, alkyl or aryl;

Y=O, S, NH or NR' where R' is an organic group with 1 to 50 carbon atoms;

a=0, 1 or 2;

b=1, 2 or 3;

c=0 or 1;

d=0 to 9;

e=0 or 1;

f=1, 2 or 3, where a+b+f=4.

The silanes of formula I are hydrolyzable by their groups X. An inorganic network with Si—O—Si units, while double bonds, spiro groups or oxirane groups contained in the R' group are polymerizing, polycondensing or polyadding by forming an organic network.

The alkyl groups are, for instance, straight chain, crosslinked or cyclic groups with 1 to 20, particularly 1 to 10 carbon atoms and, preferably, low alkyl groups having 1 to 6 and preferably 1 to 4 carbon atoms.

Particular examples are methyl, ethyl, n-propyl, I-propyl, n-butyl, I-butyl, s-butyl, t-butyl, n-pentyl, n-hexyl, cyclohexyl, 2-ethylhexyl, dodecyl and octadecyl.

The alkenyl groups are, for instance, straight chain, crosslinked or cyclic groups with 2 to 20, preferably 2 to 10 carbon atoms and, preferably, low alkenyl groups with 2 to 20 carbon atoms, such as, for instance, vinyl, allyl an d 2-butenyl.

Preferred aryl groups are phenyl, biphenyl and naphthyl. The alkoxy, acyloxy, alkylamino, dialkylamino, alkylcarbonyl, alkoxycarbonyl, arylalkyl, alkylaryl, alkene and alkenearylene groups are preferably derived from the alkyl and aryl groups referred to above.

Particular examples are methoxy, ethoxy, n- and I-propoxy, n-, I-, s- and t-butoxy, monomethylamino, dimethylamino, diethylamino, N-ethylanilino, acetyloxy, propionyloxy, methylcarbonyl, ethylcarbonyl, benzyl, 2-phenylethyl and tolyl.

The mentioned groups may be provided with one or more substituents, as required, e.g. halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, isocyano, nitro, epoxy, $SO_3H$ or $PO_4H_2$.

Among the halogens, fluorine, chlorine and bromine in particular chlorine, are the preferred ones.

Where a=2 or b≦2 the groups X and R may each have the same or a different meaning.

Without limiting generality, the following are examples of groups of index f (with d=0, 1 or 2 and linking of the phenyl units in the para-position):

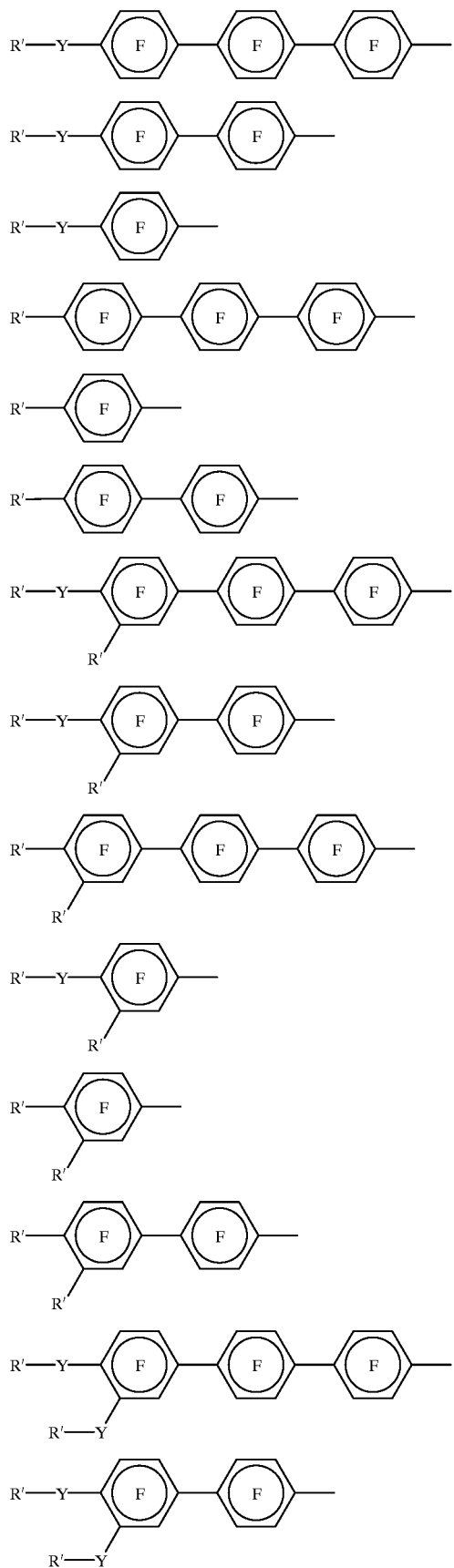
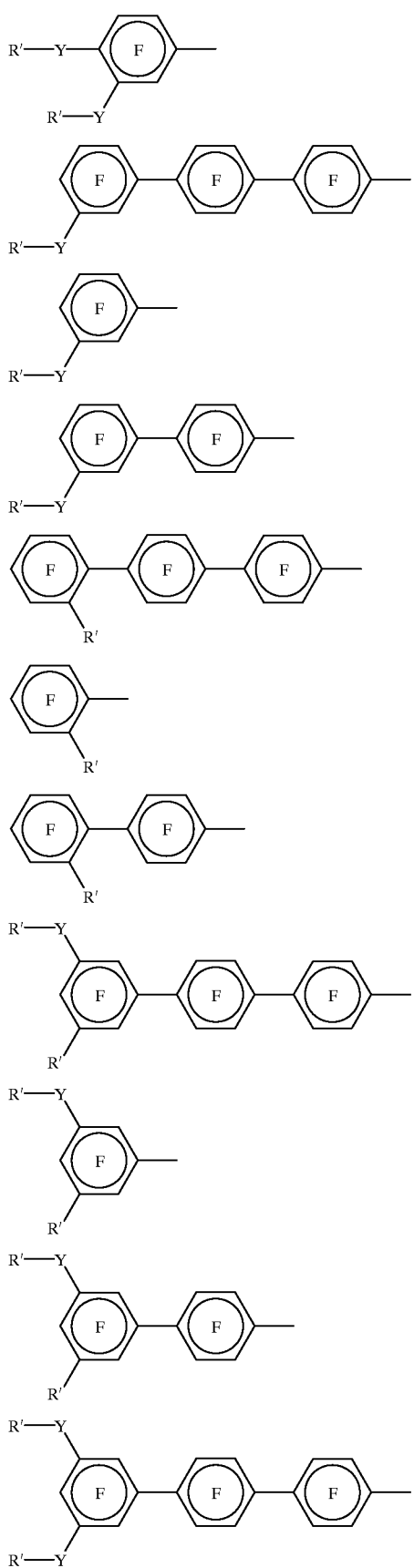

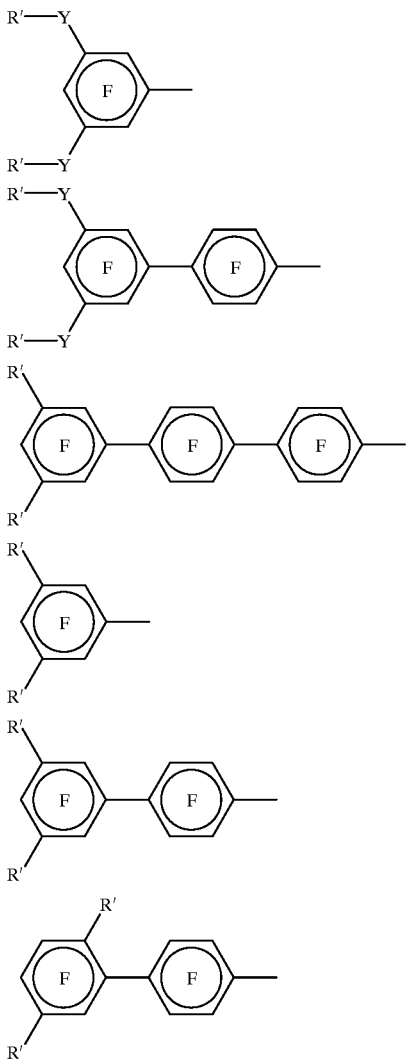

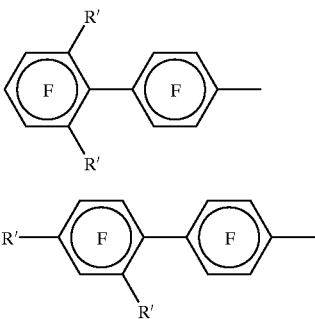

The silanes in accordance with the invention contain substituted (poly)-phenyl groups with up to 10 phenyl units, with cross-linking being possible in the ortho and/or meta and or para position. Phenylene, biphenylene and terphenylene groups are preferred. In accordance with the values stated for index f, up to three (poly)phenylene groups may be connected to the silicon atom.

The terminal position phenyl group contains up to two groups R' which are linked to the ring system by way of the ether and/or thioether and/or amino group and/or directly. Provided the terminal position phenyl groups has two substituents ortho-, meta- or para-linking is possible. If it has three substituents, they will be in the 1.2.3-, 1.2.4- or 1.3.5 position.

The group R' is an organic group having 1 to 50 carbon atoms. Preferably, group R' contains at least one C═C double bond, such as, e.g., vinyl, allyl, acryl, and/or methacryl groups, and 2 to 50, preferably 2 to 30 carbon atoms. Preferably R' contains two or more acrylate and/or methacrylate groups. The following are concrete examples of such R' groups:

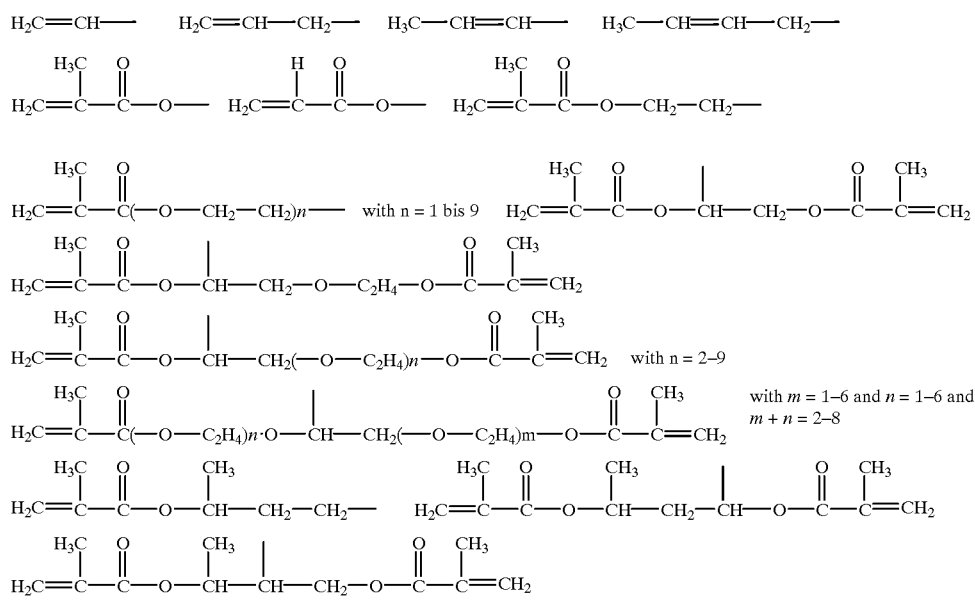

-continued
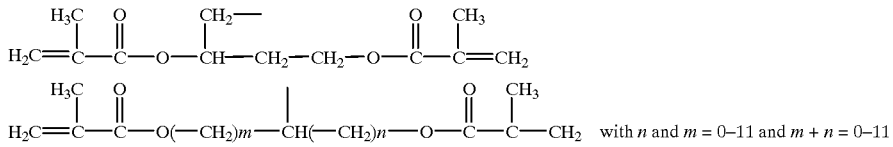
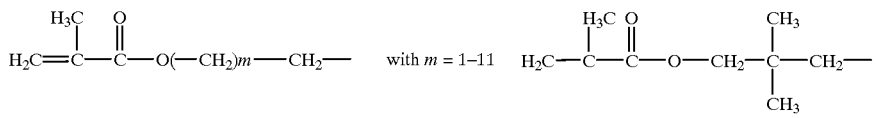
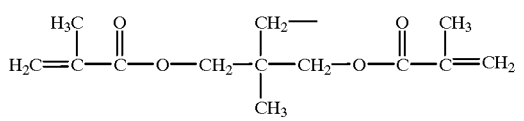
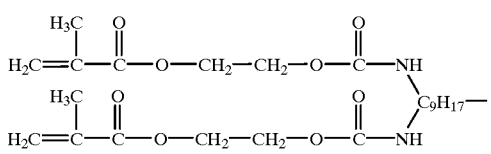
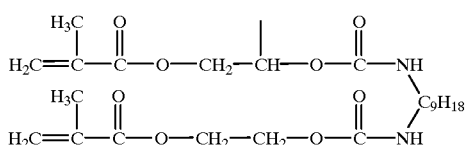
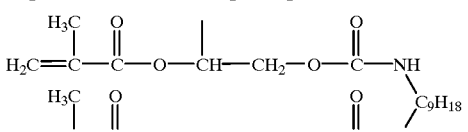
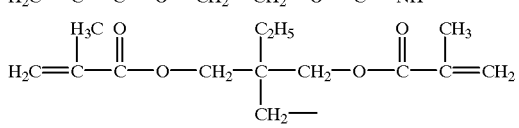
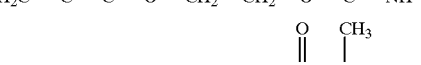
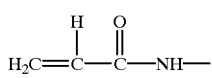
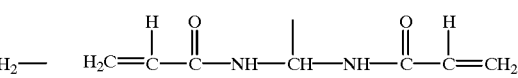
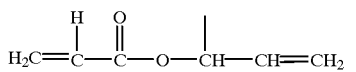
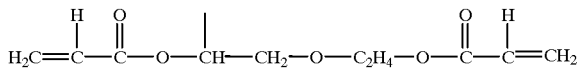
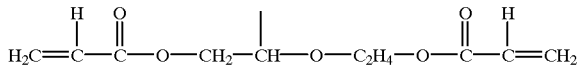
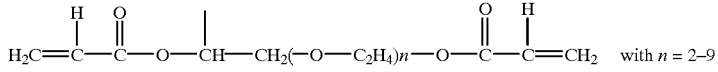
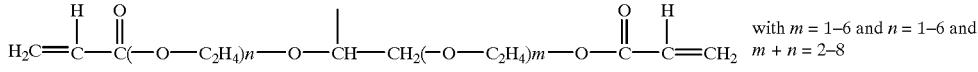
-continued
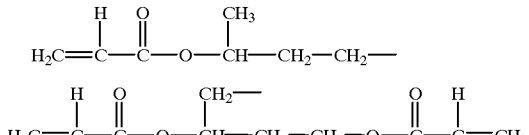
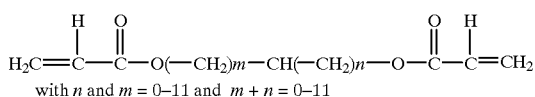
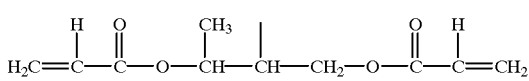

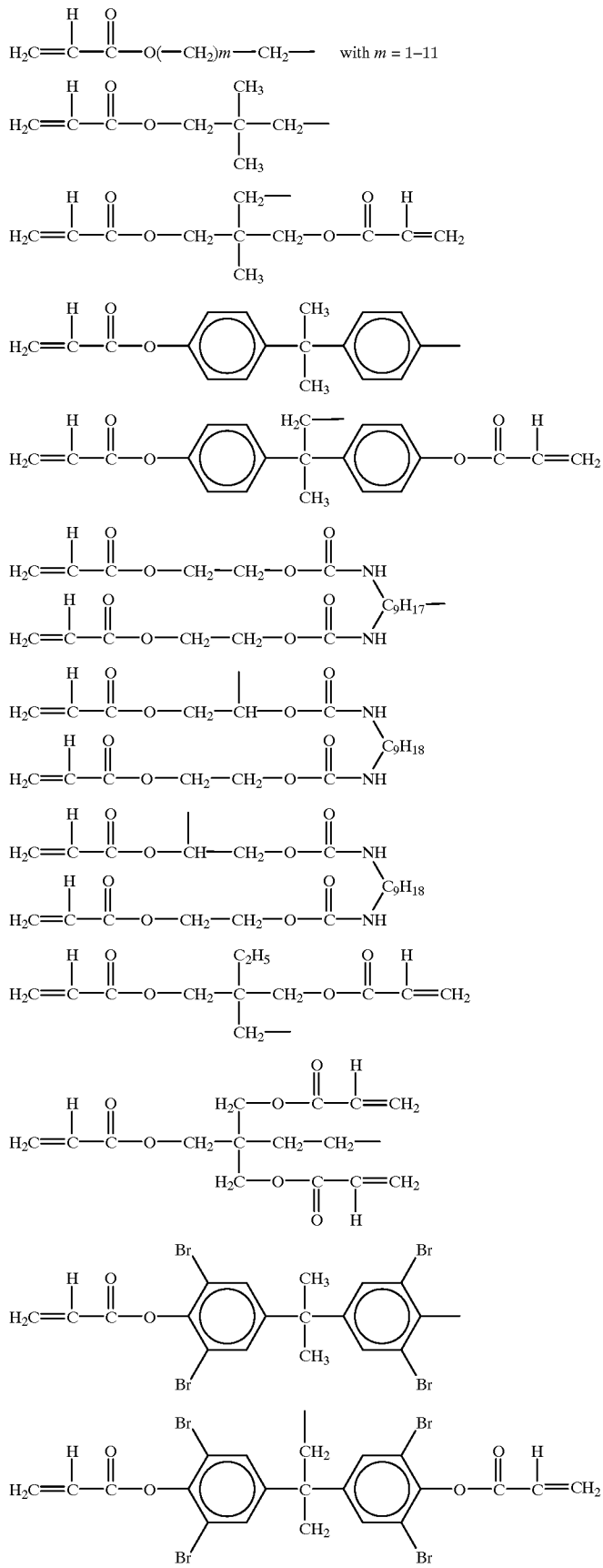

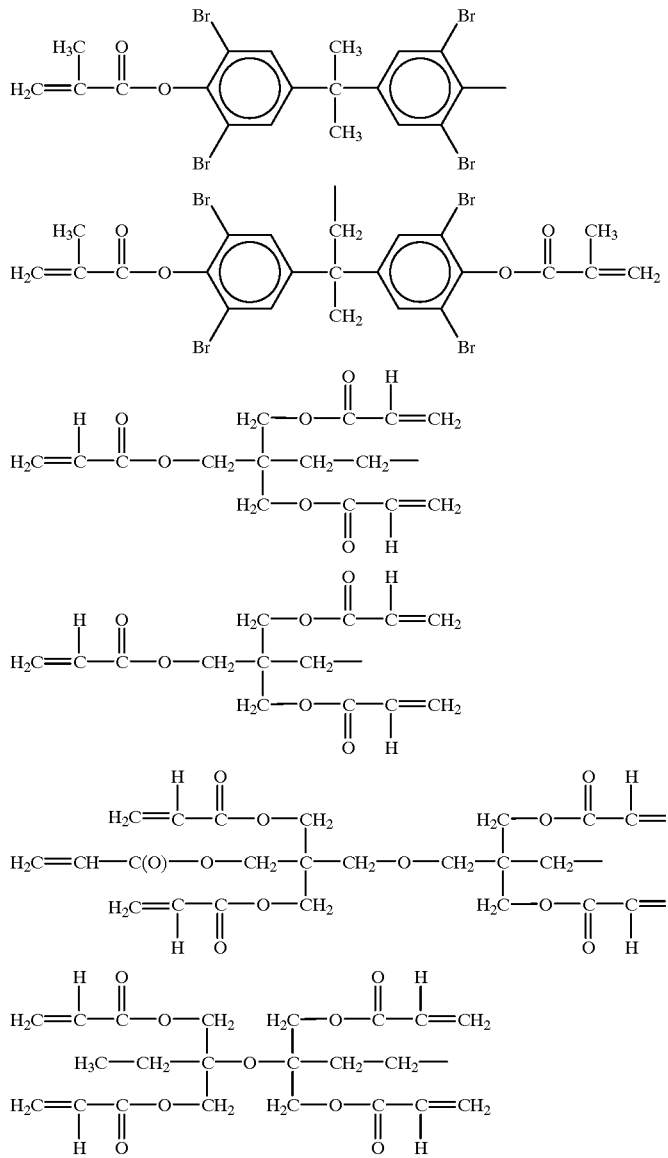
Furthermore, the group R' preferrably containes one or more spiro groups. Without limiting generality, the following are concrete examples of such R' groups:
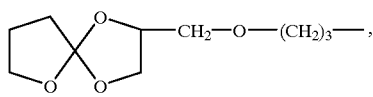
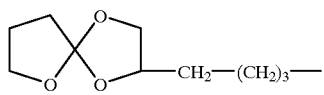
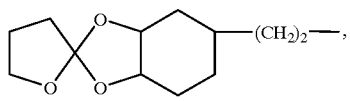
-continued
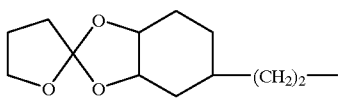
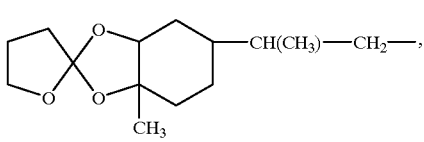
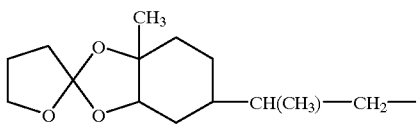

-continued

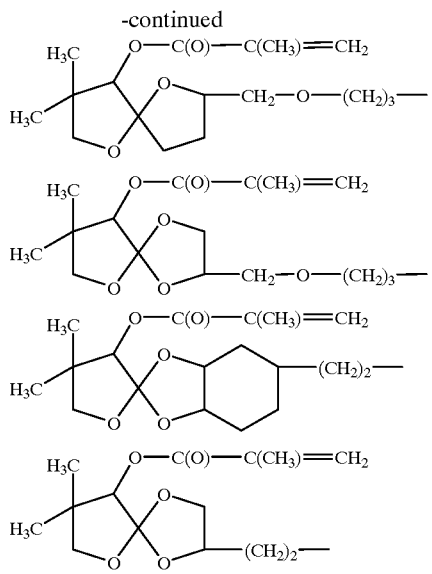

Preferably, the R' group also contains one or more substituted or unsubstituted oxirane rings. Without limiting generality, the following are concrete examples thereof:

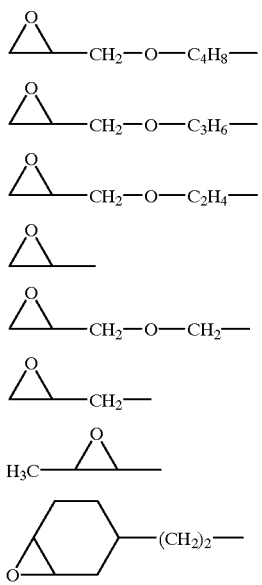

The R' group may also be a halogen, R' Br or I being always possible. Where index d of general formula I≠0, the halogen may also be F or Cl. If the hydroly-zable group X is different from hydrogen or if R is different from methyl, or if the index e=1, R' may also be hydrogen.

Further preferred embodiments of the R' group contain at least one perfluorated alkyl, alkenyl or aryl group. Without limiting generality, the following are concrete examples of such R' groups: $CF_3$, $C_2F_3$, $C_2F_5$, $i-C_3F_7$, $n-C_3F7$, $n-C_4F_9$, $i-C_4F_9$, $s-C_4F_9$ or $t-C_4F_9$.

In further embodiments, more than one silicon atom is contained in the silanes in accordance with the invention, i.e., one or more of the R' groups contain $SiR_gX_{3-g}$ or $SiR_hX_{2-h}$ groupings, where g=0, 1, 2 or 3 and h=0, 1 or 2. Where g<3 or h<2, these groups are provided with hydrolyzable X groups, and the silanes in accordance with the invention may be incorporated into an inorganic network by these groups also. Without limiting generality, the following are general formulae of such silanes:

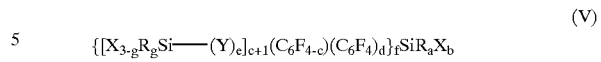 (V)

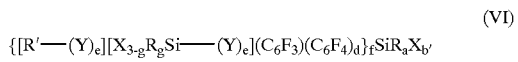 (VI)

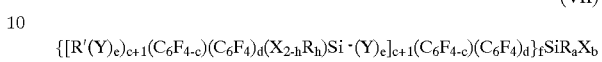 (VII)

where g=0, 1, 2 or 3 and h=0, 1 or 2, whereby the remaining groups and indices are identical or different and are defined as in general formula I.

Without limiting generality, the following are a few examples of such groups with index f (where d=1, 2 or 3 and g=2) in accordance with formulae V and VI. There may either be three hydrolyzable groups X, three non-hydrolyzable groups R or any possible combination of groups X and R provided at the silicon atom.

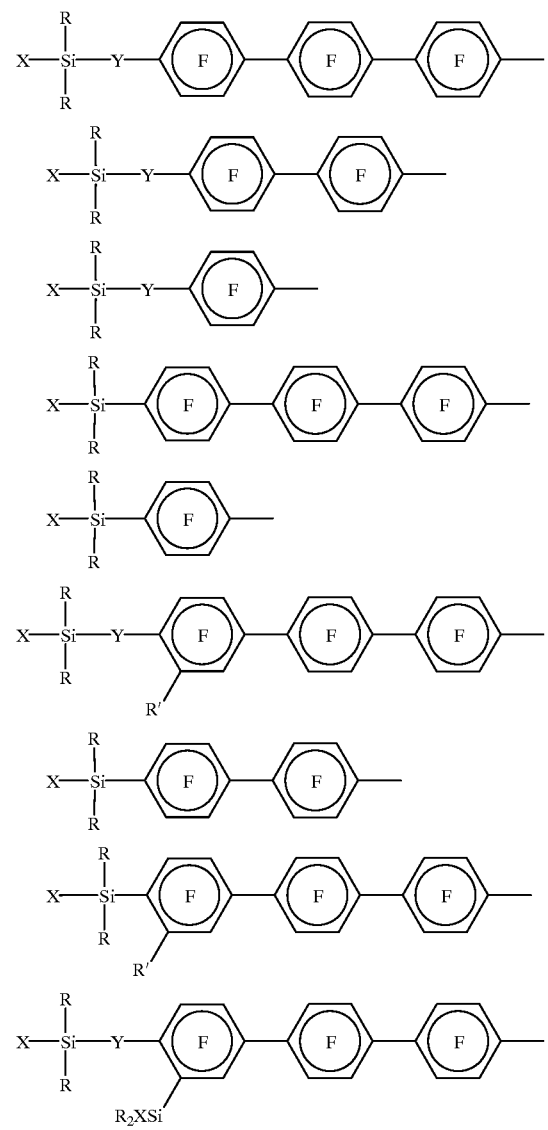

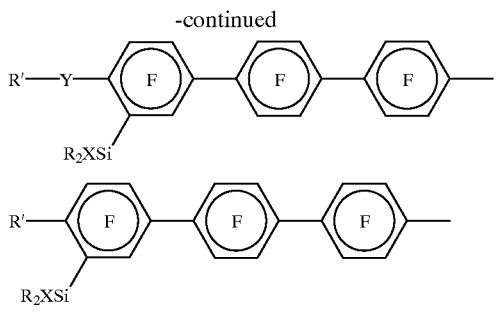
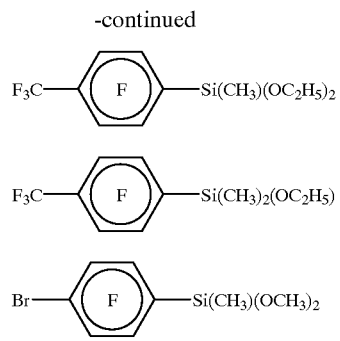
Without limiting generality, the following are concrete examples of groups having an index f in accordance with formula VII:
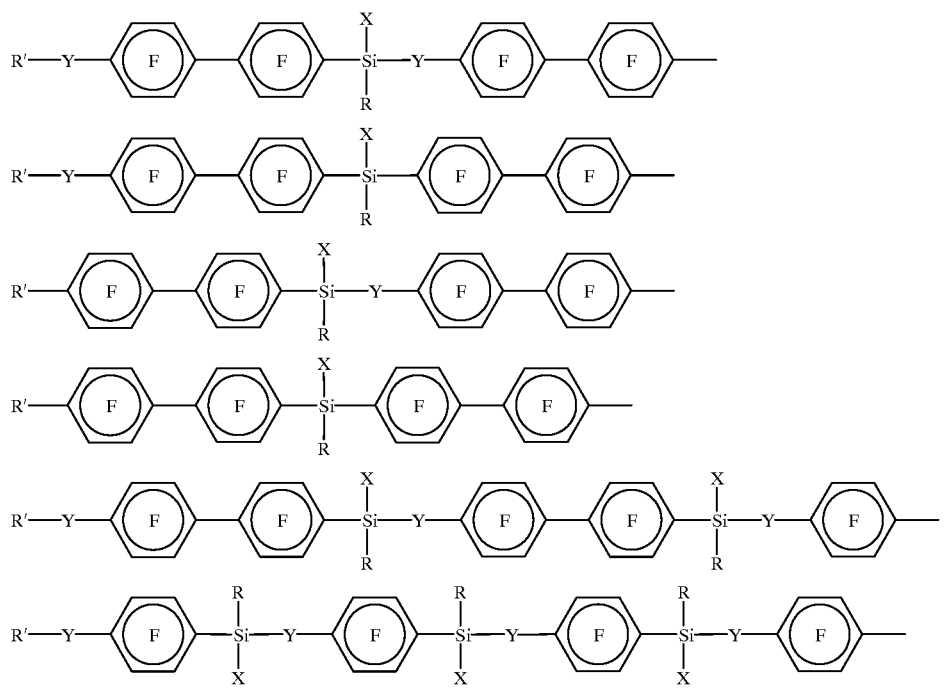
Without limiting generality, the following are concrete examples of silanes in accordance with the invention:
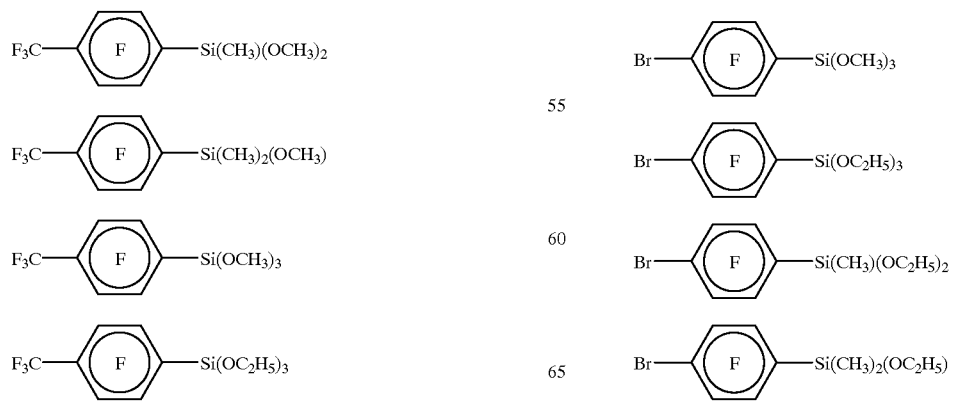

-continued (CH₃)₃SiO—⟨F⟩—Si(CH₃)(OCH₃)₂

(CH₃)₃SiO—⟨F⟩—Si(OCH₃)₃

(CH₃)₃SiO—⟨F⟩—Si(OC₂H₅)₃

(CH₃)₃SiO—⟨F⟩—Si(CH₃)₂(OCH₃)

(CH₃)₃SiO—⟨F⟩—Si(CH₃)(OC₂H₅)₂

(CH₃)₃SiO—⟨F⟩—Si(CH₃)₂(OC₂H₅)

(CH₃O)₃Si—⟨F⟩—Si(CH₃)(OCH₃)₂

(CH₃O)₃Si—⟨F⟩—Si(OCH₃)₃

(CH₃O)₃Si—⟨F⟩—Si(OC₂H₅)₃

(CH₃O)₃Si—⟨F⟩—Si(CH₃)₂(OCH₃)

(CH₃O)₃Si—⟨F⟩—Si(CH₃)(OC₂H₅)₂

(CH₃O)₃Si—⟨F⟩—Si(CH₃)₂(OC₂H₅)

H₂C=CH—⟨F⟩—Si(CH₃)(OCH₃)₂

H₂C=CH—⟨F⟩—Si(OCH₃)₃

H₂C=CH—⟨F⟩—Si(OC₂H₅)₃

H₂C=CH—⟨F⟩—Si(CH₃)₂(OCH₃)

H₂C=CH—⟨F⟩—Si(CH₃)(OC₂H₅)₂

H₂C=CH—⟨F⟩—Si(CH₃)₂(OC₂H₅)

-continued

H₂C=C(H)CH₂—⟨F⟩—Si(CH₃)(OCH₃)₂

H₂C=C(H)CH₂—⟨F⟩—Si(OCH₃)₃

H₂C=C(H)CH₂—⟨F⟩—Si(OC₂H₅)₃

H₂C=C(H)CH₂—⟨F⟩—Si(CH₃)₂(OCH₃)

H₂C=C(H)CH₂—⟨F⟩—Si(CH₃)(OC₂H₅)₂

H₂C=C(H)CH₂—⟨F⟩—Si(CH₃)₂(OC₂H₅)

F₂C=CF—⟨F⟩—Si(CH₃)(OCH₃)₂

F₂C=CF—⟨F⟩—Si(OCH₃)₃

F₂C=CF—⟨F⟩—Si(OC₂H₅)₃

F₂C=CF—⟨F⟩—Si(CH₃)₂(OCH₃)

F₂C=CF—⟨F⟩—Si(CH₃)(OC₂H₅)₂

F₂C=CF—⟨F⟩—Si(CH₃)₂(OC₂H₅)

D₂C=CD—⟨F⟩—Si(CH₃)(OCH₃)₂

D₂C=CD—⟨F⟩—Si(OCH₃)₃

D₂C=CD—⟨F⟩—Si(OC₂H₅)₃

D₂C=CD—⟨F⟩—Si(CH₃)₂(OCH₃)

D₂C=CD—⟨F⟩—Si(CH₃)(OC₂H₅)₂

D₂C=CD—⟨F⟩—Si(CH₃)₂(OC₂H₅)

-continued
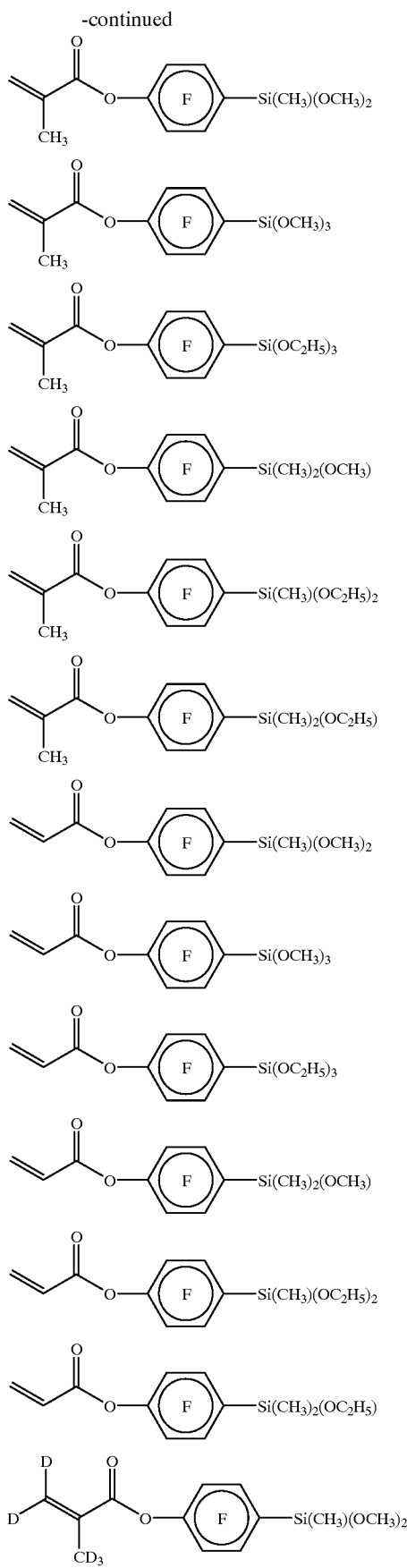
-continued
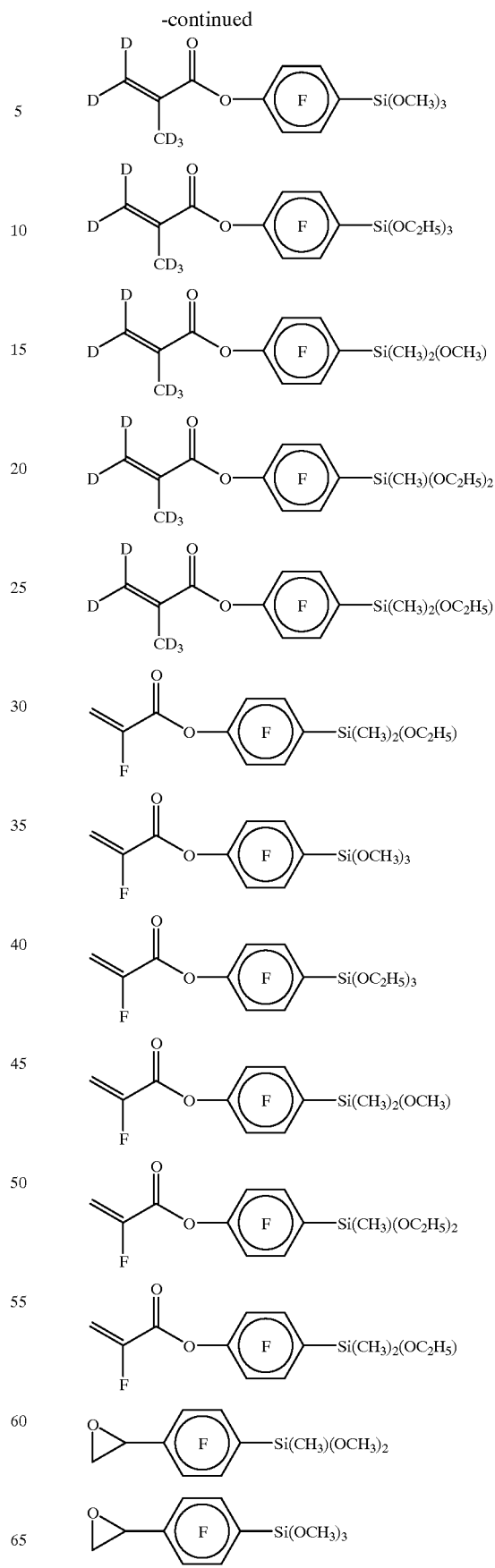

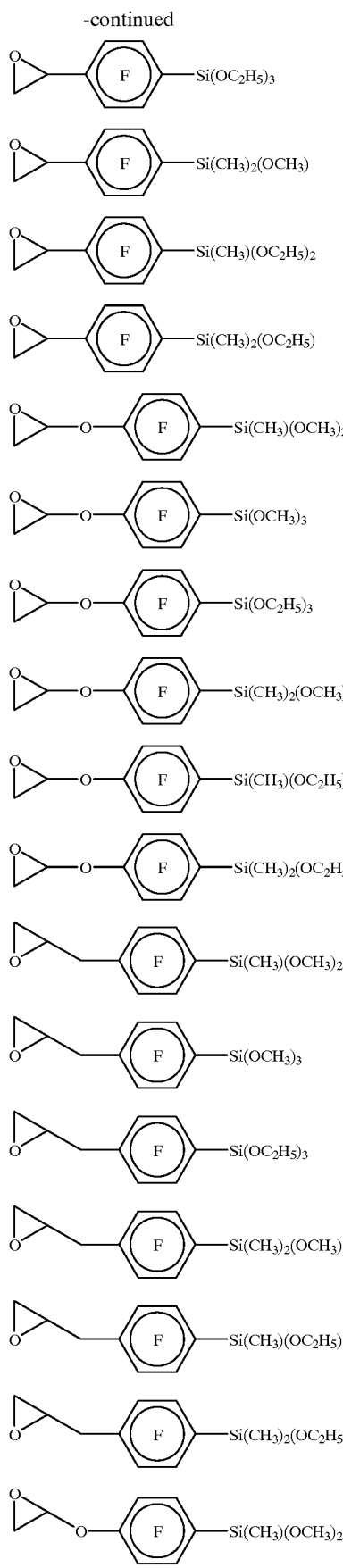
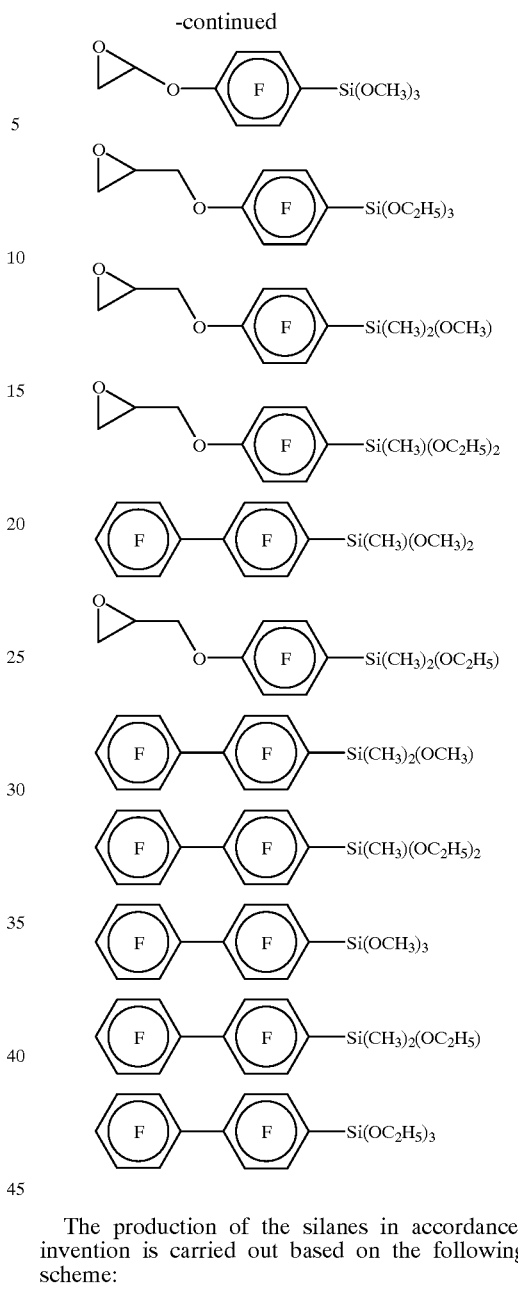

The production of the silanes in accordance with the invention is carried out based on the following reaction scheme:

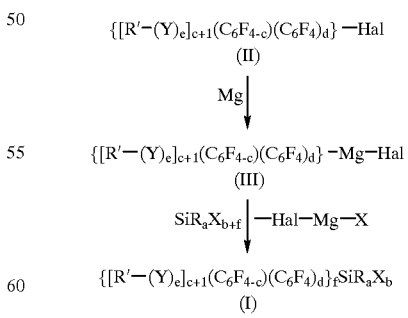

Organic halogen compounds of general formula II are converted by conventional processes with elementary magnesium to organomagnesium (Grignard) compounds of general formula III, and these, in turn, are added to silanes $SiR_aX_{b+f}$ of general formula IV, eliminating, however f mols hal-Mg-X. The groups and indices of general formulae II, III and IV are defined as in general formula I. Organic halogen compounds of general formula II are either commercially available, or they may be obtained by conventional processes of synthetic organic chemistry, as shown in the following example:

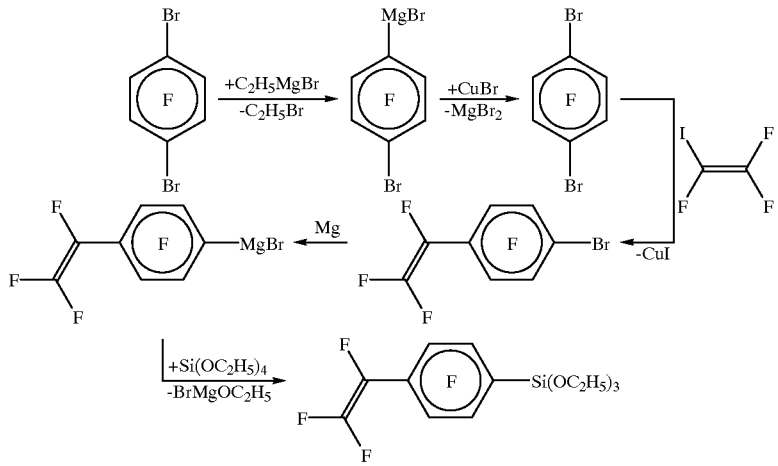

It is also possible on the basis of conventional processes of organic synthetic chemistry to prepare further silanes in accordance with the invention by modification and/or substitution of the R' group of the inventive silanes.

The silanes in accordance with the invention are stable compounds, and they may by themselves or together with other hydrolyzable, (poly)condensible and/or polymerizable and/or polyadditive compounds be processed into silicic acid polycondensates or hetero silicic acid poly-condensates the final curing of which may then be carried out by polymerization and/or polyaddition and/or polycondensation of the functional groups of the inventive silanes and/or of the applied components. However, the inventive silanes may also by themselves or together with other hydrolyzable, condensible and/or polymerizable and/or polyadditive and/or polycondensible components be processed into polymers, polyadducts or polycondensates which are then cured by hydrolytic condensation.

(Hetero) silicic acid polycondensates which may be modified with organic groups, as well as processes of their production (proceeding, for instance, from hydrolytically condensible organo-silanes on the basis of the sol-gel-process) are known in large number. As mentioned above, such condensates are used for many purposes, e.g. as formed articles, as lacquers for coatings, and so on. But because of the many possible uses of this class of substances there is always a need for modifying the condensates which are already known, on the one hand for exploring new fields of use and, on the other hand, for further optimizing their properties for defined purposes.

The silanes in accordance with the invention may be hydrolyzed and condensed in an alkaline as well as in an acidic environment. Because of this, it is possible to incorporate the inventive silanes into an inorganic-organic network by hydrolytic condensation. The silanes in accordance with the invention contain hydrolyzable X groups, e.g., alkoxy groups, so that an inorganic network may be formed therewith, whereas such functional groups as C=C double bonds, spiro groups or oxirane rings contained in the R' group may be polymerized, polyadded or polycondensed by forming an organic network. It is thus possible to replace conventional organically modified, hydrolyzable and condensible silanes in coating, filler, adhesive and caulking compounds, in formed articles and embedding compounds by silanes in accordance with the invention.

To form an inorganic network, silanes in accordance with the invention are hydrolyzed and polycondensed, if necessary by adding other cocondensible compounds. Preferably, the polycondensation is carried out by the sol-gel-process, as described, for instance, in German patent specifications DE-A1 2,758,414; 2,758,415; 3,011,761; 3,826,715 and 3,835,968.

For building the organic network, silanes in accordance with the invention are polymerized, polyadded or polycondensed, if necessary by adding other copolymerizable, polyadditive or polycondensible compounds. The polymerization may, for instance, be carried out thermically, by redox induction, covalent-nucleophilically and/or photochemically, based on processes as described, e.g., in German patent specifications DE-A1 3,143,820; 3,826,715 and 3,835,968.

Further polymerizable compounds which may be added are those which are radically and/or ionically polymerizable. Radically polymerizable compounds which may be added are, for instance, those having C=C double bonds, such as, e.g., acrylates and methacrylates, the polymerization taking place by the C=C double bonds. Ionically polymerizable compounds which may be added are, for instance, those which are provided with ring systems which are polymerizable with cationic ring scission, such as, for instance, spiro-orthoesters, spiro-orthocarbonates, bicyclic spiro-orthoesters, mono- or oligo-epoxides or spiro-silanes, as known from German patent specification DE-C1 4,125,201. But compounds may also be added, which are polymerizable ionically as well as radically, such as, e.g., methacryloyl-spiro-orthoesters. These may be radically and tonically polymerized by the C=C double bond and cationic ring scission, respectively. The production of such silanes has been described, for instance, in the Journal f. prakt. Chemie, Vol. 33, No. 2, 1988, pp. 316–318. The inventive silanes may also be sed in systems of the kind described. for instance, in German patent specification DE 4,405,261.

It is furthermore possible to add other known silane-bound cyclic systems to the polymerization. Such systems may be those containing epoxides, for instance. Such systems have been described in German patent specification DE-C1 4,125,201 in connection with the producing spirosilanes.

The silanes in accordance with the invention are, in part, highly reactive systems leading to (hetero)polycondensates which, by UV irradiation for instance, yield mechanically stable coatings or form or filler compounds within a very short time. The inventive silanes may be produced by simple reactions and may be provided with a variable number of reactive groups of different functionalities by an appropriate selection of the initial compounds.

A three-dimensional network may be built if two or more C=C double bonds are present. The mechanical properties (e.g. flexibility) and the physico-chemical properties (adsorption, refractive index, adhesion, etc.) of the (hetero) polycondensates may be influenced by way of the spacing between the Si atom and the group R', i.e. by the chain length of the phenylene units and by the presence of further functional groups. By building an inorganic network, siliconous or glassy properties of the (hetero)polycondensates may be set in accordance with the type and quantity of the hydrolyzable groups (.e.g. alkoxy groups.

The silanes in accordance with the invention have relatively high molecular weights and a correspondingly reduced volatility, as compared to pure (meth)acrylate monomers, so that any toxic hazard is reduced during processing and application. During inorganic and/or organic cross-linking, polysiloxanes with still lower volatility are formed which then completely eliminate the problem of toxicity of the acrylic compounds.

If, in addition, the possibilities for variations of the cocondensible and copolymerizable and polyadditive compounds are taken into consideration, it becomes apparent that by the inventive silanes (hetero)silicic acid polycondensates are provided which may be adapted to predetermined fields of application. For that reason, they may not only be applied to all fields in which (hetero)silicic acid polycondensates have hitherto been used, but they also open up new possibilities of use, e.g. in the areas of optics, electronics, medicine, opto-electronics, and of wrapping materials for food, etc.

The silanes in accordance with the invention may either be used as such or in compounds which additionally contain additives adapted to a particular use, e.g. common lacquer additives, solvents, fillers, photoinitiators, thermic initiators, wetting agents and pigments. The silanes in accordance with the invention or the silane-containing compounds are useful, for instance, for making, coating, filler and bulk materials, adhesives and injection molding compounds, fibers, particles, foils, bonding agents, impression and imbedding materials. Coatings and formed articles made from silanes in accordance with the invention offer the advantage of being photochemically structurable. Special fields of application are, for instance, coating by immersion, casting, brushing, spraying, electrostatic spraying, electro-dipcoating, etc., the use for optical, opto-electrical or electronic compounds, the production of fillers, the manufacture of scratch proof abrasion-resistant corrosion protection coating, the manufacture of molded, e.g. by injection molding, die casting, pressing, rapid prototyping or extrusion, and the manufacture of composites with fibers, fillers or webs, for examples.

Aside from the inventive silanes of formula I, further hydrolytically condensible compounds of silicon, boron, aluminum, phosphorus, tin, lead, transitional metals, lanthanides or actinides may be used. These materials may be used as such or in precondensed form for producing polycondensates. It is preferred, if at least 10 mol-%, in particular 80 mol-%, and especially at least 90 mol-%, based on monomeric compounds, of the basic materials used for the production of (hetero) silicic acid polycondensates are silicon compounds.

In the same manner, it is also preferred if the (hetero) silicic acid polycondensates are based upon at least 5 mol-%, e.g., 25 to 100 mol-%, more particularly 50 to 100 mol-% and especially 75 to 100 mol-%, each based monomeric compounds, one or more of the inventive silanes.

For processing the inventive silanes into (hetero) condensates, it is not actually required to isolate the inventive silanes. It is possible initially to produce the silanes by a one-pot process and then to condense them hydrolytically, if needed by added further hydrolyzable compounds.

Among the hydrolytically condensed silicon compounds different from the silanes of general formula I which may also be used, the ones of general formula VIII are especially preferred $$R_a(R''Z')_b SiX_{4-(a+b)} \qquad (VIII)$$

in which the groups R, R", x and Z' are identical or different and have the following meaning:

R=alkyl, alkenyl, aryl, alkylaryl or arylalkyl;
R"=alkylene or alkenylene, whereby these groups may be interrupted by oxygen or sulfur atoms or by —NH— groups;
X=hydrogen, halogen, hydroxy, alkoxy, acyloxy, alkylcarbonyl, alkoxycarbonyl or NR'$_2$, with R'=hydrogen, alkyl or aryl;
Z'=halogen or an amino, amide, aldehyde, alkylcarbonyl, carboxy, mercapto, cyano, alkoxy, alkoxycarbonyl, sulfonic acid, phosphoric acid, acryloxy, methacryloxy, epoxy or vinyl group, substituted if required;
a=0, 1, 2 or 3;
b=0, 1, 2 or 3, with a+b=1, 2 or 3.

Such silanes have been described, for instance, in German patent specification DE-C2 3,407,087.

The following are examples of hydrolytically condensible materials of general Formula: CH$_3$—Si—Cl$_3$, CH$_3$—Si—(OC$_2$H$_5$)$_3$, C$_2$H$_5$—Si—Cl$_3$, C$_2$H$_5$—Si—(OC$_2$H$_5$)$_3$, CH$_2$=CH—Si—(OC$_2$H$_5$)$_3$, CH$_2$=CH—Si—(OC$_2$H$_4$OCH$_3$)3, (CH$_3$)$_2$—Si—Cl$_2$, CH$_2$=CH—Si—(OOCCH$_3$)$_3$, (CH$_3$)$_2$—Si—(OC$_2$H$_5$)$_2$, (CH$_2$H$_5$)$_3$—Si—Cl, (C$_2$H$_5$)$_2$—Si—(OC$_2$H$_5$)$_2$, (CH$_3$)$_2$(CH$_2$=CH)—Si—Cl$_2$, (CH$_3$)$_3$—Si—Cl, (t—C$_4$H$_9$)(CH$_3$)$_2$—Si—Cl, (CH$_3$O)$_3$—Si—C$_3$H$_6$—NH—C$_2$H$_4$—NH—C$_2$H$_4$—NH$_2$, (CH$_3$O)$_3$—Si—C$_3$H$_6$—SH, (CH$_3$O)$_3$—Si—C$_3$H$_6$—NH—C$_2$H$_4$—NH$_2$, (CH$_3$O)$_3$—Si—C$_3$H$_6$—Cl, (CH$_3$O)$_3$—Si—C$_3$H$_6$—O—C(O)—C(CH$_3$)=CH$_2$, (CH$_3$)$_2$(CH$_2$=CH—CH$_2$)—Si—Cl, (C$_2$H$_5$O)$_3$—Si—C$_3$H$_6$—NH$_2$, (C$_2$H$_5$O)$_3$—Si—C$_3$H$_6$—CN,

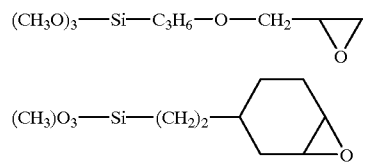

Among the hydrolytically condensible silicon compounds different from the silanes of general formula I and which, if necessary, could also be used, those of general formula IX are preferred $$\{X_n R_k Si[(R^2 A)_l]_{4-(n+k)}\}_x B \qquad (IX)$$

where groups A, R, R$^2$ and X are identical or different and have the following meaning:

A=O, S, PR', POR', NHC(o)o or NHC(O)NR', with R'=hydrogen, alkyl or aryl;

B=a straight chain or cross-linked organic group derived from a compound B' with at least one (for l=1 and A=NHC(O)O or NHC(O)NR') or at least two C=C double bonds and 5 to 50 carbon atoms;

R=alkyl, alkenyl, aryl, alkylaryl or arylalkyl;

$R^2$=alkylene, arylene or alkylenearylene;

X=hydrogen, halogen, hydroxy, alkoxy, acyloxy, alkylcarbonyl, alkoxycarbonyl or NR'$_2$;

n=1, 2 or 3;

k=0, 1 or 2;

l=0 or 1;

x=a whole integer the maximum value of which corresponds to the number of double bonds in the B' compound minus 1, or equals the number of double bonds in compound B' if l=1 and A represents NHC(O)O or NHC(O)NR';

Such silanes have been described in German and European patent specifications DE 4,011,044 and EP 91,105,355, respectively.

Among the hydrolytically condensible silicon compounds which, if needed, can also be used and which differ from the silanes of general formula I, those of general formula X are also preferred

$$X_n SiX_m R_{4-(n+m)} \quad (X),$$

in which the groups X, Y and R are identical or different and have the following meaning:

R=alkyl, alkenyl, aryl, alkylaryl or arylalkyl;

X=hydrogen, halogen, hydroxy, alkoxy, acyloxy, alkylcarbonyl, alkoxycarbonyl or NR'$_2$;

Y=a substituent containing a substituted or non-substituted 1,4,6-trioxaspiro-[4,4]-nonane group;

n=1, 2 or 3;

m=1, 2 or 3, with n+m≦4.

These spiro-silanes are hydrolyzable through the X groups and polymerizable through the Y groups and have been described in great detail in German patent specification DE-C1 4,125,201.

Among the hydrolyzable aluminum compounds which could be used, those of general formula

$AlR°_3$ are especially preferred, in which the R° groups which may be identical or different, have been selected from halogen, alkoxy, alkoxycarbonyl and hydroxy. As regards the closer (preferred) definitions of these groups, reference may be had to the explanations in connection with the usable hydrolyzable silicon compounds. The groups just mentioned may also be wholly or partially replaced by chelate ligands (e.g. acetylacetone or acetoacetic acid ester, acetic acid).

Aluminumalkoxides and halides are particularly preferred aluminum compounds. In this connection, the following may be mentioned as concrete examples:

Al(OCH$_3$)$_3$, Al(OC$_2$H$_5$)$_3$, Al(O—n—C$_3$H$_7$)$_3$, Al(O—i—C$_3$H$_7$)$_3$, Al(OC$_4$H$_9$)$_3$, Al(O—i—C$_4$H$_9$)$_3$, Al(O—s—C$_4$H$_9$)$_3$, AlCl$_3$, AlCl(OH)$_2$.

Compounds which are volatile at room temperature, such as aluminum-sec-butylate and aluminum-iso-propylate are especially preferred.

Suitable hydrolyzable titanium or zirconium compounds which may be used are those of the general formula

MX$_y$R$_z$ in which M stands for titanium or zirconium, y is a whole number from 1 to 4, especially 2 to 4, z=1, 2 or 3, preferably 0, 1 or 2, and X and R are defined as in general formula I. This holds true for the two preferred meanings as well. Particularly preferred are those compounds in which y=4.

As in the case of the above aluminum compounds, complexed Ti or Zr compounds may be used. Additional preferred complexing agents in this context are acrylic acid and methacrylic acid; silanes in accordance with the invention and provided with acrylic or methacrylic groups may also be used for the complexing. In that case the great advantage of the inventive silanes is that for complexing the Ti and Zr compounds no additional complexing agents are required.

The following are concrete examples of usable Zr and Ti compounds:

TiCl$_4$, Ti(OC$_2$H$_5$)$_4$, Ti(OC$_3$H$_7$)$_4$, Ti(O—i—C$_3$H$_7$)$_4$, Ti(OC$_4$H$_9$)$_4$, Ti(2-ethylhexoxy)$_4$, ZrCl$_4$, Zr(OC$_2$H$_5$)$_4$, Zr(OC$_3$H$_7$)$_4$, Zr(O—i—C$_3$H$_7$)$_4$, Zr(OC$_4$H$_9$)$_4$, Zr(2-ethylhexoxy)$_4$, ZrOCl$_2$.

Further hydrolyzable compounds which may be used for producing heteropolycondensates are, e.g., boron trihalides and boric acid esters such as, e.g., BCl$_3$, B(OCH$_3$)$_3$ and B(OC$_2$H$_5$)$_3$, stannic halides and stannic alkoxides such as, e.g., SnCl$_4$ and Sn(OCH$_3$)$_4$ and vanadium compounds such as, e.g., VOCl$_3$ and VO(OCH$_3$)$_3$.

As already mentioned, the production of the (hetero) polycondensates may be accomplished in the manner which is conventional in this field. If, for all intents and purposes, only silicon compounds are used, the hydrolytic condensaion may in most cases take place by directly adding the water required at room temperature or slightly cooled (preferably by stirring and in the presence of a hydrolytic and condensation catalyst) to the silicon compounds to by hydrolyzed which are present either as such or dissolved in an appropriate solvent, and by thereafter stirring the resultant mixture for some time (one to several hours).

In the presence of reactive compounds of Al, Ti or zr a step-wise addition of the water is usually recommended. Regardless of the reactivity of the compounds present, the hydrolysis usually takes place at temperatures between −20 and 130° C., preferably between 0 and 30° C., or at the boiling point of any solvent used. As already indicated, the best mode of adding water is dependent above all upon the reactivity of the initial compounds used. Thus, the dissolved initial compounds may be slowly dripped into excess water, or the water is added to the initial compounds which may be dissolved either in a batch or in drops. It may also be advantageous, not to add the water as such, but, rather, by adding it to the reaction system by means of aqueous organic or inorganic systems. In many instances, it has been found to be particularly advantageous to add the water to the reaction mixture by means of moisture-laden adsorbents, e.g. molecular sieves, and aqueous organic solvents, e.g. 80% ethanol. However, the adding of water may also be accomplished by a chemical reaction in which the water is released during the reaction. Esterifications are examples thereof.

If a solvent is used, ketones, preferably lower dialkylketones such as acetone or methylisobutylketone, ethers, preferably lower dialkylethers such as diethylether or dibutylether, THF, amides, esters, in particular acetic acid ethylester, dimethylformamide, amines, in particular triethylamine, and their mixtures may be considered aside from lower aliphatic alcohols (e.g. ethanol or 1-propanol).

Where spiro-silanes are applied for producing (hetero) polycondensates, the hydrolysis is preferably performed in an environment which is basic relative to the spiro-silane.

This may be provided by a basic solvent such as, e.g., triethylamine, or by adding basic hydrolysis and condensation catalysts such as, e.g., $NH_3$, NaOH, KOH, methylimidazole, etc.

The initial compounds need not necessarily all be present at the beginning of the hydrolysis (polycondensation); rather, in certain circumstances it may be advantageous to add water to only some of these compounds and later to add the remaining compounds.

In order as far as possible to prevent sedimentations during the hydrolysis and polycondensation when using hydrolyzable compounds different from silicon compounds, water may be added in several, e.g., three stages. To this end, one tenth to one twentieth of the quantity of water needed for the hydrolysis may be added during the first stage. After brief stirring, one fifth to one tenth of the required quantity of water may be added; and following another brief stirring the remainder may at last be added.

The condensation time is dependent upon the initial compounds and the quantitative proportions, any catalyst used, the reaction temperature, and so on. Generally, the reaction is carried out at normal pressure; it may, however, also be performed at increased or at reduced pressure.

The (hetero)polycondensate thus obtained may be processed further either in the state in which it has been obtained or after removal of some or substantially all of the used solvents. In some cases, it may be advantageous to replace any excess water or any solvent formed or added in the product obtained by the polycondensation by another solvent in order to stabilize the (hetero)polycondensate. To this end, the reaction mixture may be thickened, e.g. in a vacuum at a slightly elevated temperature, to the point at which it can still be received in another solvent without any problem.

Where these (hetero)polycondensates are to be used as lacquers for coating (e.g. of plastics such as PVC, PC, PMMA, PE, PS, etc., of glass, paper, wood, ceramics, metal, etc.) conventional lacquer additives such as, e.g. coloring agents (pigments or dyes), fillers, oxidation inhibitors, flame retardants, wetting agents, UV absorbers, stabilizers and the like, may be added thereto no later than immediately prior to their application. Mention may also be made of additives for increasing the conductivity (e.g. graphite powder, silver powder, etc.). Where they are to be used as molding compounds, the addition of inorganic and/or organic fillers is possible, such as, e.g., organic and inorganic particles, fiberglass, fibers, minerals, etc.

Final curing of the (hetero)polycondensates is carried out thermally, by redox induction, covalentnucleophilically or photo-chemically. Several curing mechanisms may be applied simultaneously and/or successively. During polymerization, polyaddition or polycondensation C=C double bonds, spiro groups or oxirane rings are linked, and the organic network is being formed. Because of the relatively high molecular weights of the silanes in accordance with the invention they will experience small volume shrinkage only.

It is also possible, prior to its final curing, i.e. prior to the polymerization, to add further ionically and/or radically polymerizing compounds to the (hetero)polycondensate. Radically polymerizable compounds which may be added are those having C=C double bonds, such as acrylates and methacrylates, the polymerization taking place at the C+C double bonds. Ionically polymerizable compounds which may be added are those which contain ring systems which may be polymerized cationically by ring scission, such as spiro-orthoesters, spiro-orthocarbonates, bicyclic spiro-orthoesters, mono- and oligoepoxides or spiro-silanes of general formula X. However, compounds may also be added which are polymerizable cationically as well as radically, such as, e.g., methacryloyl-spiro-orthoesters. These may be polymerized radically by way of their C=C double bonds and cationically by ring scission. Such systems have been described, for instance, in the Journal f. prakt. Chemie (Journal of Practical Chemistry), Vol. 330, No. 2, 1988, pp. 316–318, or in the Journal of Polymer Science: Part C: Polymer Letters, Vol. 26, S. 517–520 (1988).

If curing takes place photochemically, photo initiators will be added; with thermic curing, thermic initiators are added; and with redox-induced curing starter-activator systems are added.

In initiator may be added in usual quantities. For instance, a mixture containing 30 to 50% by weight of solids (polycondensate) may thus have added to it initiators in a quantity of from .0.5 to 5% by weight, preferably from 1 to 3% by weight, based on the mixture.

If aside from the silanes in accordance with the invention, further compounds containing reactive double bonds, such as, e.g. silanes of general formula IX, are used for the production of the (hetero)polycondensates, a thermically and/or photochemically and/or covalent-nucleophilic and/or redox-induced polymerization may also proceed by these double bonds.

Commercially available photo initiators may be used. Examples of such photo initiators thereof are, for instance, Irgacure 184 (1-hydroxycyclohexylphenylketone), Irgacure 500 (1-hydroxycyclohexylphenylketone/benzophenone) and other Irgacure type photo initiators available from Ciba-Geigy; Darocure 1173, 1116, 1398, 1174 and 1020 (available from the Merck Co.), benzophenone, 2-chlorothioxanthone, 2-methylthioxanthone, 2-isopropylthioxanthone, benzoin, 4.4'-dimethoxybenzoin, etc.

Usable thermic initiators are, in particular, organic peroxides such as diacylperoxides, peroxydicarbonates, alkylperesters, dialkylperoxides, perketals, ketoneperoxides and alkylhydroperoxides. Concrete and preferred examples of thermic initiators are dibenzoylperoxide, t-butylperbenzoate and azobisisobutyronitrile.

The usual starter/activator systems may be used, such as aromatic amines;(e.g. N,N-bis-(2-hydroxy-ethyl)-p-toluidine) as activators or, as a starter, dibenzoylperoxide, for instance, the curing time being settable in accordance with a particular application by their concentration or ratio of concentration. Further amines have been described, for instance, in German patent specification DE 4,310,733.

Compounds with at least one amine group, for instance, may be used for covalent-nucleophilic curing. Suitable amines have been described for instance in German patent specification DE 4,405,261.

A lacquer ((hetero)polycondensate) based on silanes in accordance with the invention and provided with an initiator may be used for coating substrates. The usual methods may be employed for such coating, such as, for instance, immersion, flooding, pouring, spinning, rolling, spraying, brushing, electrostatic spraying and elector-dipping. It should here be mentioned that the lacquer need not necessarily contain any solvent. Especially when initial substances (silanes) having two alkoxy groups on their Si atom are used it is possible to work without adding solvents.

Prior to curing the applied lacquer is preferably dried. Thereafter and depending upon the type of initiator, it may be cured in a known manner by redox induction, thermically or photochemically. Combinations of curing methods are, of course, possible.

If curing is carried out by irradiation, it may be advantageous to carry out thermic curing after curing by irradiation, especially to remove any remaining solvents or to incorporate further reactive groups into the curing process.

Even though polymerizable groups may already be present in (hetero)polycondensates base on silanes in accordance with the invention, it may in some circumstances be advantageous prior to or during their further processing (curing) to add further compounds (preferably purely organic ones) with unsaturated groups to these condensates. Preferred examples of such compounds are acrylic acid and methacrylic acid as well as compounds derived therefrom, especially esters of preferably monovalent alcohols (e.g. $C_{1-4}$-alkanol), (meth)acrylnitrile, styrene and mixtures thereof. In case the (hetero)polycondensates are used for producing coating lacquers, such compounds may at the same time function as solvents and thinners.

The production of formed articles or molding compounds from (hetero)polycondensates based upon silanes in accordance with the invention may be carried out by any process common in this field such as, for instance, pressing, injection molding, die casting, extrusion, etc. The (hetero) polycondensates based on inventive silanes may also be used for making composite materials (for instance with fiber glass reinforcement).

The inventive silanes may also be used for producing hydrolytically condensible polymers, polyadducts or polycondensates. To this end, the inventive silanes are polymerized, polyadded or polycondensed either by themselves or together with other radically and/or ionically polymerizable, polyadditive or polycondensible compounds, any terminal curing taking place by hydrolytic condensation by way of the hydrolyzable groups of the inventive silanes and any further hydrolyzable compounds.

In such a case, the organic network is first built by polymerization, followed by hydrolytic condensation to build the inorganic network.

The production of the polymers is carried out by radical and/or ionic polymerization of one or more C═C double bond containing compounds and any other radically and/or ionically polymerizable compounds. It is, preferably, redox induced and/or covalent-nucleophilic and/or by heat and/or by electromagnetic radiation, if need be in the presence of one or more initiators and/or solvents, and is characterized by 5 to 100 mol-%, based on monomeric compounds, of the C═C double bond containing compounds are selected from the inventive silanes of general formula I.

It is, however, also possible, prior to their polymerization to add further Ionically and/or radically polymerizable compounds to the silanes in accordance with the invention. Radically polymerizable compounds which ay be added are, for instance, those having C═C double bonds, such as, e.g. acrylates or methacrylates, the polymerization taking place at the C═C double bonds. Ionically polymerizable compounds which may be added contain ring systems, for instance, which are polymerizable cationically by ring scission, such as, for instance, spiro-orthoesters, spiro-orthocarbonates, bicyclic spiro-orthoesters, mono- and oligo-epoxides or spiro-silanes of general formula X. Compounds may also be added, however, which are polymerizable cationically as well as radically, such as, e.g., methacryloyl-spiro-orthoesters. These may be polymerized radically through their C═C double bonds and cationically by ring scission. Such systems have been described in Journal f. prakt. Chemie (Journal of Practical Chemistry), Vol. 330, No. 2, 1988, S. 316–318 or in the Journal of Polymer Science: Part C: Polymer Letters, Vol. 26, pp. 517–520 (1988).

Furthermore, additional hydrolyzable and polymerizable silicon compounds may be added to the inventive silanes, if needed in precondensed form, which are then incorporated in the polymerization. Such silicon compounds are derived from epoxy-containing silanes, for instance; they are thus cationically polymerizable and are used for making spirosilanes of the kind described in German patent specification DE-C1 4,125,201. These systems have been described in German patent specification DE 4,125,201.

It is also possible to use silicon compounds which are derived from those of general formula IX and which are radically polymerizable. These systems have already been described in detail in connection with the production of the (hetero)polycondensates.

The polymerization is carried out covalent-nucleophilically and/or by redox induction and/or thermically and/or photochemically after suitable initiators have been added. In the course of a radical polymerization C═C double bonds are cross-linked and ring scission occurs of spiro groups and of any further radically polymerizable rings during any cationic polymerization. It has surprisingly been found that during the course of this polymerization the volume of the reaction mass does not change or changes insignificantly only. The reason for this is seen in the relatively high molecular weight of the silanes in accordance with the invention.

If polymerization takes place photochemically photo initiators will be added to the reaction mass; if polymerization takes place thermically, thermic initiators will be added; and in case of redox induced polymerization a starter/activator system will be added.

Where compounds including spiro groups have been added to the inventive silanes, a thermically or photochemically inducible polymerization may also occur through these compounds. Commercially available photoinitiators may be used.

The initiator may be added in conventional quantities. Thus, a quantity of 0.5 to 5% by weight, more particularly 1 to 3% by weight, of initiator, based on the mixture, may be added to a mixture, for instance, which contains 30 to 50% by weight of solids (polycondensate).

The polymer, polyadduct or polycondensate obtained in this manner may be hydrolytically condensed for building an inorganic network, if need be in the presence of further hydrolytically condensible silicon compounds and other elements of the group consisting of B, Al, P, Sn, Pb, the transitional metals, the lanthanides and the actinides and/or of precondensates derived from the compounds mentioned above, by the effect of water or moisture. If required, a catalyst and/or solvent may also be present. The polymers contain hydrolyzable groups X, e.g. alkoxy groups so that an inorganic network (Si—O—Si units) may be built with them.

Among the hydrolyzable silicon compounds which may be used, those of general formula VIII are preferred.

These systems have already been described in detail in connection with the production of (hetero)polycondensates and associated with concrete examples.

Among the used hydrolyzable aluminum compounds the ones of general formula $AlR°_3$ are preferred, and suitable hydrolyzable titanium and zirconium compounds which may be used are those of general formula $Mx_yR_z$. These systems, too, have already been described in detail in connection with the production of (hetero)polycondensates.

Further hydrolyzable compounds which may be added to the polymer, polyadduct or polycondensate are, e.g. boron trihalides and boric acid esters, such as, e.g., $BCl_3$, B(OCH$_3$)$_3$ and B(OC$_2$H$_5$)$_3$, stannic halides and stannic alkoxides, such as, e.g., SnCl$_4$ and Sn(OCH$_3$)$_4$, and vadium compounds, such as, e.g., VOCl$_3$ and VO(OCH$_3$)$_3$.

Here too, as has already been mentioned, the hydrolytic condensation may be performed in the manner customary in this field. In most cases, the hydrolytic condensation may be carried out by adding the required water at room temperature or slightly cooled to the hydrolyzable polymer, polyadduct or polycondensate as such or dissolved in a suitable solvent. Preferably, the water is added by stirring and in the presence of a hydrolysis and condensation catalyst.

In the presence of reactive compounds of Al, Ti or Zr a step-wise addition of the water is usually recommended. Regardless of the reactivity of the compounds present, the hydrolysis usually takes place at temperatures between −20 and 130° C., preferably between 0 and 30° C., or at the boiling point of any solvent used. As already indicated, the best mode of adding water is dependent above all upon the reactivity of the initial compounds used. Thus, the dissolved polymer may be slowly dripped into excess water, or the water is added to the polymer which may be dissolved, either in a batch or in drops. It may also be advantageous not to add the water as such, but, rather, to introduce it into the reaction system by means of aqueous organic or inorganic systems.

Owing to their surprisingly good solvability in conventional solvents compared to polyfluoroalkyl silanes, and because of their hydrolysis/condensation properties the polyfluoroaryl silanes in accordance with the invention are excellently suited as precursors for the production of fluorinated organo polysiloxane lacquers. The siloxane lacquers made with silanes of the invention are easily handles and are suitable for producing optically transparent formed articles, surface layers, etc. Materials are obtained with low optical attenuation which may be used in optical data processing, in telecommunications and in structuring and connection technology (e.g. as buffers, cores, cladding, optical switches, distributors and amplifiers). The materials produced with silanes of the invention are compatible for structuring, connecting and thin film technologies, they may be structured and replicated photo lithographically.

It has surprisingly been found that production of fluorinated polysiloxane lacquers by means of the inventive silanes is easily accomplished without requiring the production of solutions of silanes in special solvents, as is the case with polyfluoroalkyl silanes. The inventive silanes may be mixed without problems with conventional organoalkoxy silanes and in standard solvents (e.g. ether, ethanol, acetone, alkane, etc.). For that reason they are excellently suited for the synthesis of (hetero) silicic acid polysiloxanes. In the same fashion, it is possible to process the inventive silanes together with conventional fluoroaryl silanes.

The lacquers produced with silanes of the invention are suitable for the production of formed articles as well as for the production of surface coatings. In their optical transparency, (hetero) silicic acid polycondensates made with silanes in accordance with the invention are far superior to conventional (hetero)silicic acid polycondensates and possess significantly improved values of attenuation. Lacquers made with inventive silanes have excellent shelf life and may be cured as needed.

The inventive polyfunctional silanes provide starter compounds with which vastly differing inorganic-organic compound polymers may be made having properties which may be set over wide ranges or which allow modifications of existing compound polymers. Such materials may be used for many different applications such as, among others, as bulk materials, composites, adhesives, sealing compounds, coating materials, bonding agents and binders for ceramic particles (ceramic forming process), for producing or piming fillers and fibers, of grinding discs. They may also be used in reaction extruders, etc. Photochemically, thermically as well as chemically (two component, anaerobic, redox, etc.) induced conversions may be used for their organic polymerization. The combination of self-curing with photo-induced or thermic curing is also possible.

The production of silanes in accordance with the invention and their use for producing (hetero) silicic acid polycondensates will be explained in detail by exemplary embodiments.

Example 1

Synthesis of p-vinyl-tetrafluorophenyl-triethoxysilane

Reaction Scheme:

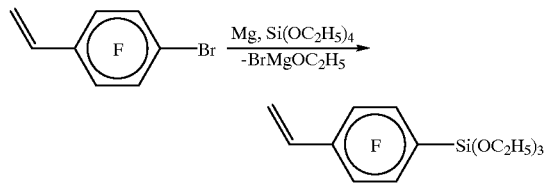

25.5 g (100 mmol) 4-bromine-2.3.5.6-tetrafluorostyrene, 4.86 g (200 mmol) magnesium chips, 125.0 g (600 mmol) tetraethoxy silane and about 4 g 1.2-dibromoethane are mixed in 150 ml ether and reflux heating until an exothermic reaction occurs. Within one hour further portions of 1.2 dibromoethane (total of 18.79 g =100 mmol) are added, and upon completion of an exothermic reaction reflux heating is continued for 16 hours. After cooling the magnesium salts which have developed are precipitated by adding n-heptane and filtered out; the solvent is removed by destillation. The residue is fractionally destined in vacuum. Identification was accomplished by IR-, $^1$H-NMR-, $^{13}$C-NMR- and $^{19}$F-NMR- spectroscopy and elementary analysis.

Yield: 11.84 g (35%);

Boiling Point: 67° C. (0.1 mbar)

Example 2

Synthesis of methacrylic acid-[4-(triethoxysilyl)]-tetrafluorophenylester Reaction Scheme:

Reaction Scheme:

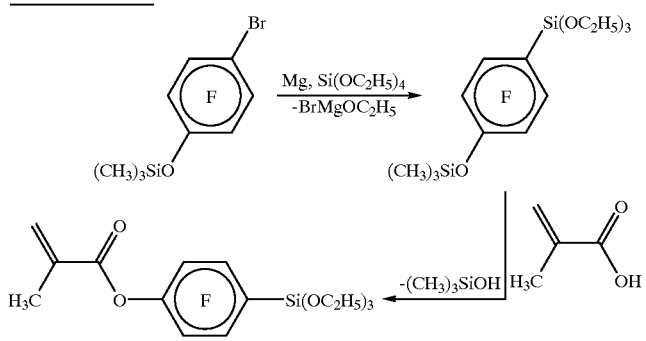

31.72 g (100 mmol) (4-bromine-2.3.5.6-tetrafluorophenoxy)-trimethylsilane, 4.86 g (200 mmol) magnesium chips, 125.0 g (600 mmol) tetraethoxysilane and about 4 g 1.2-dibromoethane are mixed in 150 ml ether and reflux heated until an exothermic reaction occurs. Within one hour further portions of 1.2 dibromoethane (total 18.79 g = 100 mmol) are added, and following completion of the exothermic reaction reflux heating continues for 16 hours. After cooling to room temperature the magnesium chips which have developed are precipitated by adding n-heptane, removed by filtering, and the solvent is removed by distillation. The residue is fractionally distilled in vacuum.

Yield : 12.41 g (31%) (p-triethoxysilyl)-tetrafluorophenoxy-trimethylsilane; Boiling Point: 80° C (0.1 mbar) 12.02 g (30 mmol) (p-triethoxysilyl)-tetrafluorophenoxytrimethylsilane and 36.86 g (800 mmol) ethanol are reflux heated for 1.5 hours. After complete removal of the solvent in a vacuum the raw product obtained is dissolved in 40 ml trichloroethane and 2.53 g pyridine are added at 0° C. Then, 3.35 g (32 mmol) methacrylic acid are dripped in at 0° C., and thereafter the mixture is stirred at room temperature for 16 hours. After filtering of the resultant precipitation the solvent is removed by distillation and the residue is fractionally distilled in a vacuum. Identification is accomplished by IR-, $^1$H-NMR-, $^{13}$C-NMR- and $^{19}$F-NMR-spectroscopy and elementary analysis.

Yield: 8.56 g (72%) methacrylic acid-[4-(triethoxy-silyl)]-tetrafluorophenylester. Boiling Point: 95° C. (0.1 mbar)

EXAMPLE 3

Preparation of a partially fluorinated organopolysiloxane lacquer from

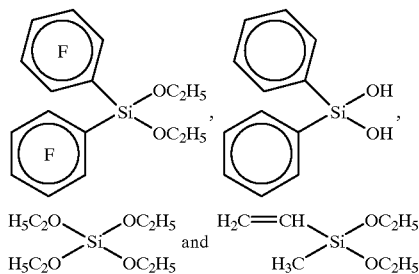

A mixture of 20 mmol dipentafluorophenyldiethoxysilane, 20 mmol vinylmethyldiethoxysilane, 5 mmol diphenylsilanediol and 5 mmol tetraethoxysilane are hydrolyzed and condensed with 95 mmol water.

EXAMPLE 4

Preparation of a highly fluorinated organopolysiloxane lacquer from

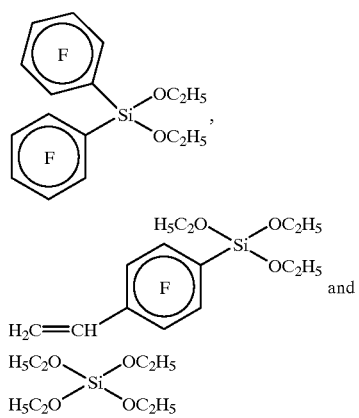

A mixture of 30 mmol dipentafluorophenyldiethoxysilane, 20 mmol p-vinyl-tetrafluorophenyl-triethoxysilane and 5 mmol tetraethoxysilane are hydrolyzed and condensed in 140 mmol water.

What is claimed is:

1. Silanes of general formula I

$$\{[R'-(Y)_e]_{c+1}(C_6F_{4-c})(C_6F_4)_d\}_f SiR_a X_b \tag{I}$$

in which the groups and indices are identical or different and have the following meaning:

R=alkyl, alkenyl, aryl, alkylaryl or arylalkyl, substituted if required, each with 1 to 15 carbon atoms, whereby the groups may be interrupted by oxygen or sulfur atoms, ester, carbonyl, amide or amino groups;

R'=I, Br, Cl (if d≠0), F (if d≠0), H (if X≠H or R≠methyl or e=1) or an organic group with 1 to 50 carbon atoms;

X=hydrogen, halogen except fluorine, hydroxy, alkoxy, acyloxy, alkylcarbonyl, alkoxycarbonyl or NR"$_2$, with R"=hydrogen, alkyl or aryl;

Y=O, S, NH or NR', where R' is an organic group with 1 to 50 carbon atoms;

a=0, 1 or 2;

b=1, 2 or 3;

c=0 or 1;
d=0 to 9;
e=0 or 1;
f=1, 2 or 3, with a+b+f=4.

2. The silanes of claim 1, wherein at least one of the groups R' contains at least one C=C double bond.

3. The silanes of claim 1, wherein at least one of the groups R' contains at least one spiro group.

4. The silanes of claim 1, wherein at least one of the groups R' contains at least one substituted oxirane group.

5. The silanes of claim 1, wherein at least one of the groups R' contains at least one non-substituted oxirane group.

6. The silanes of claim 1, wherein at least one of the groups R' contains at least one group from the class comprising perfluorated alkyl, alkenyl and aryl.

7. The silanes of claim 1, wherein at least one of the groups R' is one of $SiR_hX_{2-h}\{(C_6F_4)_d(C_6F_{4-c})[(Y)_e-R']_{c+1}\}$ and $SiR_gX_{3-g}$, where g=0, 1, 2 or 3 and h=0, 1 or 2 and whereby the remaining groups and indices are identical or different as defined in claim 1.

8. A silicic acid polycondensate derived from a silane of claim 1 by hydrolytic condensation of at least one hydrolytically condensible silicon compound with one of water and moisture, wherein 1 to 100 mol-%, based on monomeric compounds, of the hydrolytically condensible compounds are selected from silanes of general formula I.

9. The silicic acid polycondensate of claim 8, including the hydrolytic condensation of compounds of the group comprising B, Al, P, Sn, Pb, the transitional metals, the lanthanides and the actinides.

10. The silicic acid polycondensate of claim 9 including the hydrolytic condensation of precondensates derived from at least one of said hydrolytically condensible compounds.

11. The silicic acid polycondensate of claim 10 wherein said hydrolytically condensible compounds are at least one of a polyadditive, polymerizable and polycondensible compound.

12. The silicic acid polycondensate of claim 11, wherein said hydrolytically condensible compound is precondensed.

13. The silicic acid polycondensate of claim 8, further comprising at least one hydrolytically condensible aluminum compound of formula AlR°, wherein R° is one of halogen, hydrogen, alkoxy and acyloxy.

14. The silicic acid polycondensate of claim 8, further comprising a hydrolytically condensible compound of one of titanium and zirconium of formula $M_xR_z$, wherein M is titanium or zirconium, R and X are identical or different and defined as in general formula I and wherein y is a whole integer from 1 to 4 and z is 0, 1, 2 or 3.

15. The silicic acid polycondensate of claim 8, including a polymerizable compound.

16. The silicic acid polycondensate of claim 8, including a polyadditive compound.

17. The silicic acid polycondensate of claim 8, including a polycondensible compound.

18. A method of producing the silanes of claim 1, wherein compounds of general formula II $$\{[R'-(Y)_e]_{c+1}(C_6F_{4-c})(C_6F_4)_d\}\text{-hal} \qquad (II)$$

where hal means halogen and the remaining groups and indices are identical or different and as defined in claim 1, are converted with elementary magnesium into Grignard compounds of general formula II $$\{[R'-(Y)_e]_{c-1}(C_6F_{4-c})(C_6F_4)_d\}\text{-Mg-hal}$$

and wherein said Grignard compounds are reacted with silanes of general formula IV $$SiR_aX_{b+f} \qquad (IV)$$

wherein the groups and indices are identical or different and are defined as in claim 1, while eliminating hal-Mg-X.

* * * * *